US005752925A

United States Patent [19]

Beaupré et al.

[11] Patent Number: 5,752,925

[45] Date of Patent: May 19, 1998

[54] INCREASING BONE FRACTURE RESISTANCE BY REPEATED APPLICATION OF LOW MAGNITUDE FORCES RESEMBLING TRAUMA FORCES

[75] Inventors: Gary S. Beaupré, Sunnyvale; Dennis R. Carter, Stanford, both of Calif.; Wilson C. Hayes, Lincoln, Mass.

[73] Assignee: Board of Trustees of the Leland Stanford Junior University, Palo Alto, Calif.

[21] Appl. No.: 661,976

[22] Filed: Jun. 12, 1996

[51] Int. Cl.[6] ........ A61N 1/00

[52] U.S. Cl. ........ 601/98; 606/239

[58] Field of Search ........ 606/1, 237–241; 128/898; 601/96, 97, 98

[56] References Cited

U.S. PATENT DOCUMENTS

| | | | |
|---|---|---|---|
| 1,617,593 | 2/1927 | Hardy | 606/239 |
| 5,103,806 | 4/1992 | McLeod et al. . | |
| 5,191,880 | 3/1993 | McLeod et al. . | |
| 5,376,065 | 12/1994 | McLeod et al. . | |
| 5,545,177 | 8/1996 | Coseo | 606/239 |

OTHER PUBLICATIONS

G. S. Beaupré, T. E. Orr, and D. R. Carter, *An Approach for Time–Dependent Bone Modeling and Remodeling—Theoretical Development*, Journal of Orthopedic Research 8(5), 1990, pp. 651–661.

G. S. Beaupré, T. E. Orr, and D. R. Carter, *An Approach for Time–Dependent Bone Modeling and RemodelinG—Application: A Preliminary Remodeling Simulation*, Journal of Orthopedic Research, 8(5), 1990, pp. 672–670.

*Primary Examiner*—Michael Buiz
*Assistant Examiner*—William W. Lewis
*Attorney, Agent, or Firm*—Lumen Intellectual Property Services

[57] ABSTRACT

The invention presents a method and device for increasing the fracture resistance of a bone tissue to a traumatic force. The method includes the step of selecting a nonphysiological impulse force having a location and direction resembling that of the traumatic force, but having a magnitude significantly smaller than the magnitude of the traumatic force. The impulse force is then repeatedly applied to the bone tissue, thereby stimulating the bone tissue to grow bone mass in critical areas where stresses from the traumatic force are largest. A device for applying the method includes an impulse force applicator for repeatedly applying the impulse force and a positioner for positioning the impulse force relative to the bone tissue.

22 Claims, 7 Drawing Sheets

| REFERENCE NUMERAL | BONE DENSITY (GRAMS/CC) |
|---|---|
| 12 | < 0.3 |
| 14 | 0.3 - 0.6 |
| 16 | 0.6 - 0.9 |
| 18 | 0.9 - 1.2 |
| 20 | > 1.2 |
| 22 | CARTILAGE |

| REFERENCE NUMERAL | STRESS STIMULUS |
|---|---|
| 30 | VERY LOW |
| 32 | LOW |
| 34 | MEDIUM |
| 36 | HIGH |
| 38 | VERY HIGH |

| REFERENCE NUMERAL | BONE DENSITY (GRAMS/CC) |
|---|---|
| 12 | < 0.3 |
| 14 | 0.3 - 0.6 |
| 16 | 0.6 - 0.9 |
| 18 | 0.9 - 1.2 |
| 20 | > 1.2 |
| 22 | CARTILAGE |

INCREASING BONE FRACTURE RESISTANCE BY REPEATED APPLICATION OF LOW MAGNITUDE FORCES RESEMBLING TRAUMA FORCES

FIELD OF THE INVENTION

This invention relates to techniques for strengthening bone tissue. More particularly, it relates to techniques for increasing the resistance of bone tissue to potential fractures.

BACKGROUND OF THE INVENTION—DESCRIPTION OF PRIOR ART

Although treatment programs have been developed for the general stimulation of bone tissue growth, these treatment programs are inadequate for substantially increasing the fracture resistance of the bone tissue. For example, a method and device for promoting general bone tissue growth is described in U.S. Pat. No. 5,376,065 issued to Macleod et al. on Dec. 27, 1994. The method includes the step of applying a mechanical load to the bone tissue to create a relatively low level of bone tissue strain between 50 and 500 microstrain. The load is applied at a relatively high frequency in a range of 10 to 50 hertz.

A device for applying such a mechanical load to the bone tissue has a platform on which a patient sits or stands. A linear actuator then oscillates the platform at a high frequency so that the patient's entire body is displaced vertically. The patient is moved through a vertical displacement of 0.01 to 2.0 mm so that his body experiences a vertical acceleration between 0.05 g to 0.5 g, producing a strain in the patient's bone tissue between 50 and 500 microstrain. Macleod found that such mechanical loading prevents bone loss and enhances new bone formation.

Although such mechanical loading may enhance new bone formation, it does not significantly increase the fracture resistance of the bone tissue. The forces that are likely to cause bone tissue fracture are not typical physiological forces. They are non-physiological or traumatic forces that occur during a traumatic event, such as an accident or fall. The vertical shaking of Macleod's method only builds dense bone tissue in areas required for withstanding the typical physiological forces experienced during normal daily activities. It does little to build bone tissue in areas needed to resist bone fracture during a traumatic event.

Another conventional method for promoting general bone tissue growth includes the use of ultrasound to stimulate the bone tissue. This method has the same disadvantage as Macleod's method in that ultrasound simulates typical physiological forces on the patient's bone tissue. It does little to increase the fracture resistance of the bone tissue to a traumatic force.

Thus, none of the prior approaches for stimulating bone tissue growth provide a method or device for developing bone mass and bone density in critical areas needed for resisting fracture during a traumatic event. None of the existing methods apply forces to the bone tissue that resemble these traumatic forces. As a result, no existing method or device increases bone density at the specific locations in the bone tissue that experience the greatest stresses during an accident or fall. Consequently, the bone tissue is still likely to fracture during such an event.

OBJECTS AND ADVANTAGES OF THE INVENTION

In view of the above, it is a primary object of the present invention to provide a method for increasing the fracture resistance of bone tissue to forces resulting from a traumatic event. In particular, it is an object of the present invention to increase bone density at the specific locations in the bone tissue where stresses resulting from a traumatic force are greatest. It is an additional object of the invention to provide a device that will safely and efficiently promote such bone tissue growth.

These and other objects and advantages will become more apparent after consideration of the ensuing description and the accompanying drawings.

SUMMARY OF THE INVENTION

The invention presents a method and device for increasing the fracture resistance of a bone tissue to a traumatic force, such as the force created by an accident or fall. The traumatic force applied to the bone tissue during such an event has a first location, first direction, and first magnitude. The method includes the step of selecting a non-physiological impulse force having a second location and second direction resembling the location and first direction, respectively, of the traumatic force. However, the impulse force is selected to have a second magnitude significantly lower than the first magnitude of the traumatic force. According to the method, the non-physiological impulse force is then repeatedly applied to the bone tissue, whereby the bone tissue is stimulated to grow bone mass in critical areas of the bone tissue where stresses from the traumatic force are largest.

In the preferred embodiment, the second location, second direction, and second magnitude of the non-physiological impulse force can be selected in part by performing a finite element analysis of the bone tissue. Also in the preferred embodiment, the second magnitude is selected in dependence upon data correlated to the present state of the bone tissue, such as the genotype and metabolic status of the patient as well as radiological or ultrasonic measurements of the bone tissue.

The invention further includes a device for increasing the fracture resistance of a bone tissue to a traumatic force in accordance with the method described above. The device has an impulse force applicator, such as a linear actuator, for repeatedly applying a non-physiological impulse force to the bone tissue. The applicator is designed to repeatedly apply the non-physiological impulse force at a second location and second direction resembling the first location and first direction, respectively, of the traumatic force. However, the non-physiological impulse force applied by the applicator has a second magnitude significantly smaller than the first magnitude of the traumatic force. The device further includes a positioner for positioning the impulse force applicator relative to the bone tissue while the non-physiological impulse force is repeatedly applied so that the bone tissue experiences the repeated applications of the non-physiological impulse force.

In the preferred embodiment, the device has a selective control panel for controlling the impulse force applicator and positioner so that the second magnitude, second direction, and second location of the non-physiological impulse force are selected through the control panel. Additionally, the control panel has buttons for controlling the frequency and number of repetitions of the non-physiological impulse force. In a particularly advantageous embodiment, the impulse force applicator has a padded impact surface for preventing the non-physiological impulse force from damaging other tissue surrounding the bone tissue. Additionally, the impulse force applicator has a feedback sensor for preventing the non-physiological impulse force from exceeding the selected second magnitude.

DETAILED DESCRIPTION

Figure 1:
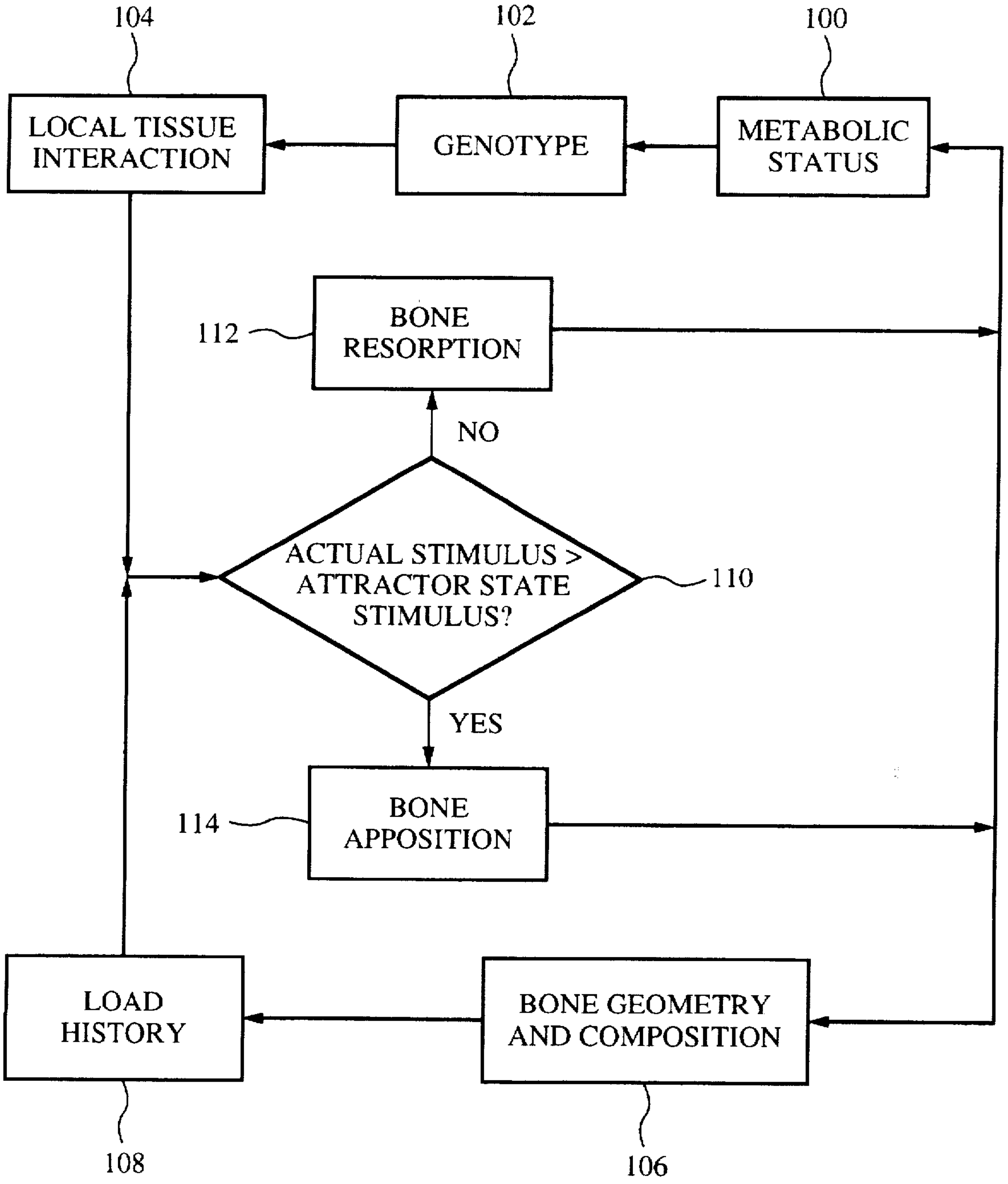
FIG. 1 is a block diagram illustrating the interaction of the key factors causing bone apposition and bone resorption.

The strength or fracture resistance of bone tissue depends upon both the quantity of bone at a specific location and the quality of bone at that location. To resist a potential fracture, bone tissue must have sufficient mass and density at the precise locations that experience the greatest stresses when a force is applied to the bone tissue. The bones of the skeleton are well designed to withstand the typical physiological forces that occur during normal daily activities, such as walking, rising from a chair, or stair climbing. During an accident or fall, however, the bones of the skeleton experience non-physiological or traumatic forces having a significantly larger magnitude than the typical physiological forces.

In addition to having a larger magnitude, these traumatic forces have a different direction and are applied to the bone tissue at a different location than the typical physiological forces. For example, during a fall to the side, the bone tissue of the femur experiences a force applied to the greater trochanter at a direction approximately perpendicular to the vertical axis of the femur. None of the typical physiological forces exerted by normal daily activity resemble this traumatic force. Because these traumatic forces have a different magnitude, direction, and location than the typical physiological forces, the bones of the skeleton often cannot withstand them. As a result, these traumatic forces fracture the bone tissue at the specific locations where stresses from the traumatic forces are greatest.

The key to increasing the fracture resistance of bone tissue is to stimulate bone apposition in the critical areas of the bone tissue where stresses resulting from a traumatic force will be largest. The factors influencing general bone apposition and bone resorption are described in Beaupré et al. "An approach for Time Dependent Bone Modeling and Remodeling—Theoretical Development", Journal of Orthopedic Research, 8:651–661, 1990, which is incorporated by reference herein. The general bone remodeling theory disclosed in Beaupré et al. does not teach a practical method for increasing the fracture resistance of bone tissue. However, it provides a useful theoretical model for predicting general bone tissue responses to typical physiological forces placed on the bone tissue in the course of normal daily activities.

The bone remodeling theory of Beaupré et al. is based upon the concept that the bone density at a particular skeletal location is dependent upon an actual daily stress stimulus $\phi_b$ experienced by the bone tissue at that location. If the bone tissue experiences insufficient stimulation, it will resorb. If the bone tissue experiences excess stimulation, additional bone will be deposited. Daily stress stimulus $\phi_b$ is defined as $$\phi b = \left( \sum_{\text{day}} n_i \sigma_{b_i}^m \right)^{1/m}$$

where $n_i$ is the number of repetitions of load type i, $\sigma_{b_i}$ is the true bone tissue level effective stress, and stress exponent m is an empirical constant. The stress exponent m is a weighting factor for the relative importance of the stress magnitude and the number of load repetitions $n_i$. Increasing values of exponent m indicate an increasing importance of the load magnitude in determining stress stimulus $\phi_b$. Whalen et al. "Influence of Physical Activity on the Regulation of Bone Density", Journal of Biomechanical Engineering, 21:825–837, 1988, found exponent m to be in the range of 3 to 8 through correlation with experimental data. Because exponent m>1, load magnitude plays a more important role than the number of load repetitions $n_i$ in determining stress stimulus $\phi_b$.

If the net rate of change in bone density due to bone apposition and bone resorption is near zero, an equilibrium condition exists. In this state, stress stimulus $\phi_b$ is approximately equal to a constant called an attractor state stimulus $\phi_{as}$. The term "attractor state" refers to the principle that many biological systems are attracted to certain target or attractor states, although these states may never be reached. If there is a difference between stress stimulus $\phi_b$ and the attractor state stimulus $\phi_{as}$, the difference yields a bone remodeling error E, expressed mathematically as $E=\phi_b-\phi_{as}$. Error E is the driving force for bone remodeling. If stress stimulus $\phi_b$ exceeds attractor state stimulus $\phi_{as}$ so that remodeling error E>0, bone apposition occurs. If stress stimulus $\phi_b$ is less than attractor state stimulus $\phi_{as}$ so that remodeling error E<0, bone resorption occurs.

The factors contributing to actual daily stress stimulus $\phi_b$ and attractor state stimulus $\phi_{as}$ are shown schematically in FIG. 1. Attractor state stimulus $\phi_{as}$ is influenced by three non-stress factors shown in the upper loop: metabolic status 100, genotype 102, and local tissue interaction 104. Metabolic status 100 refers to the current state of the metabolism of the patient to whom the bone tissue belongs. It is affected by drugs, hormones, and disease. Genotype 102 refers to demographic information about the patient, such as age, sex, and vasculature. Local tissue interaction 104 refers to various local non-stress effects, such as surgical insult, that affect attractor state stimulus $\phi_{as}$. Actual daily stress stimulus $\phi_b$ is determined in the lower loop from a bone geometry and composition 106 and a load history 108. The combination of bone geometry and composition 106 and load history 108 determine actual stress stimulus $\phi_b$ experienced by the bone tissue.

Once the attractor state stimulus $\phi_{as}$ and actual stress stimulus $\phi_b$ have been determined, they are compared in decision block 110. If actual stress stimulus $\phi_b$ is greater than attractor state stimulus $\phi_{as}$, then bone apposition 114 occurs, and the bone tissue becomes more dense. If actual stress stimulus $\phi_b$ is less than attractor state stimulus $\phi_{as}$, then bone resorption 112 occurs, and the bone tissue becomes less dense. Changes in bone density due to apposition or resorption feed back into both the upper and lower loops and influence subsequent osteoblastic and osteoclastic action.

As mentioned previously, the bone remodeling theory of Beaupré et al. presents a useful theoretical model for predicting local bone tissue response to typical physiological forces experienced by the bone tissue. However, a bone tissue fracture occurs as a result of the traumatic forces applied to the bone tissue, not as a result of the typical physiological forces. The inventors recognized that this model could be extended to include traumatic forces and that bone fractures could be prevented by creating a specific treatment program that increased bone density in the critical areas required to withstand these traumatic forces.

Figure 2:
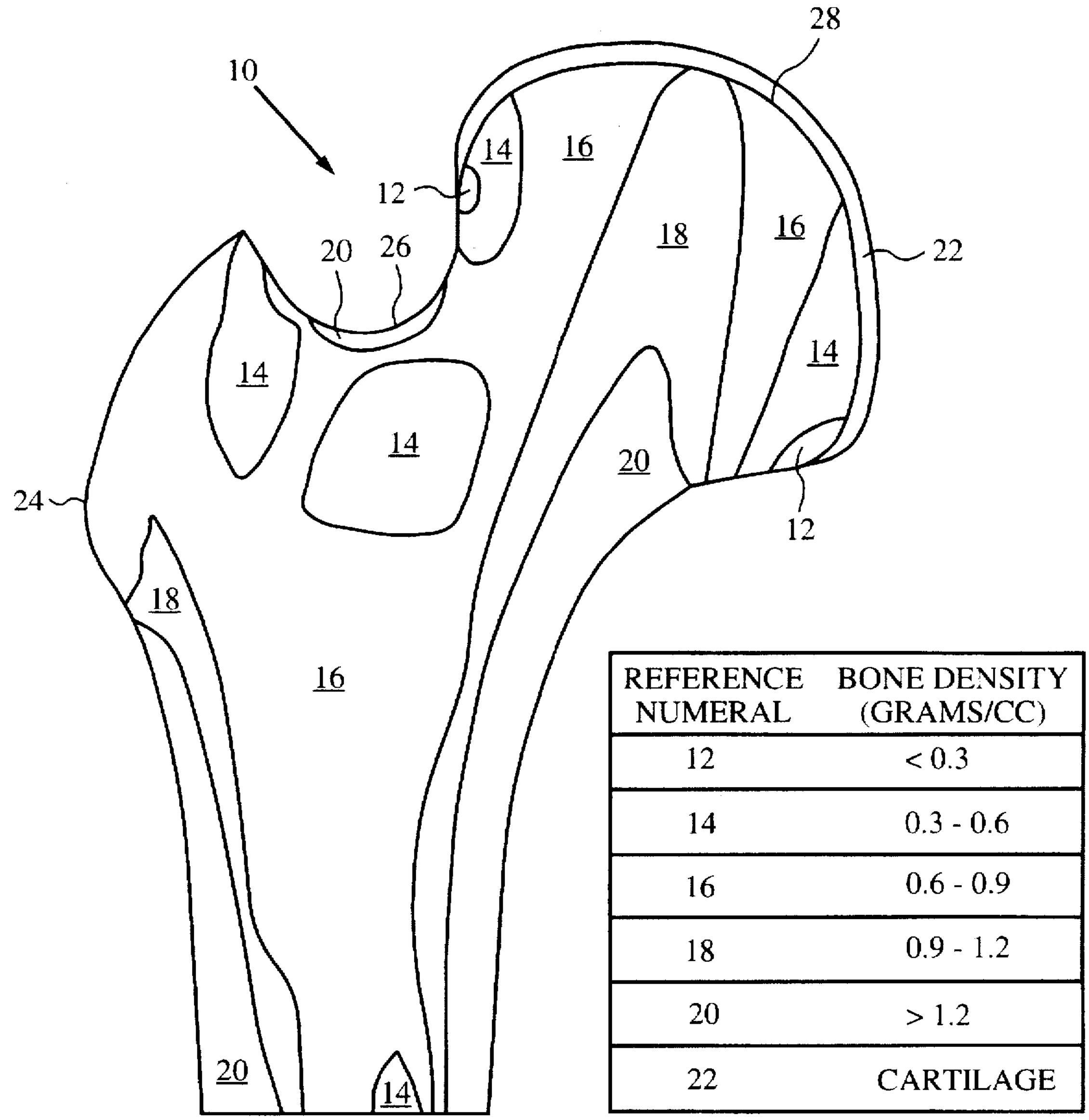
FIG. 2 is a schematic view of the normal bone densities in the proximal femur before applying the method and device of the invention.
Figure 3:
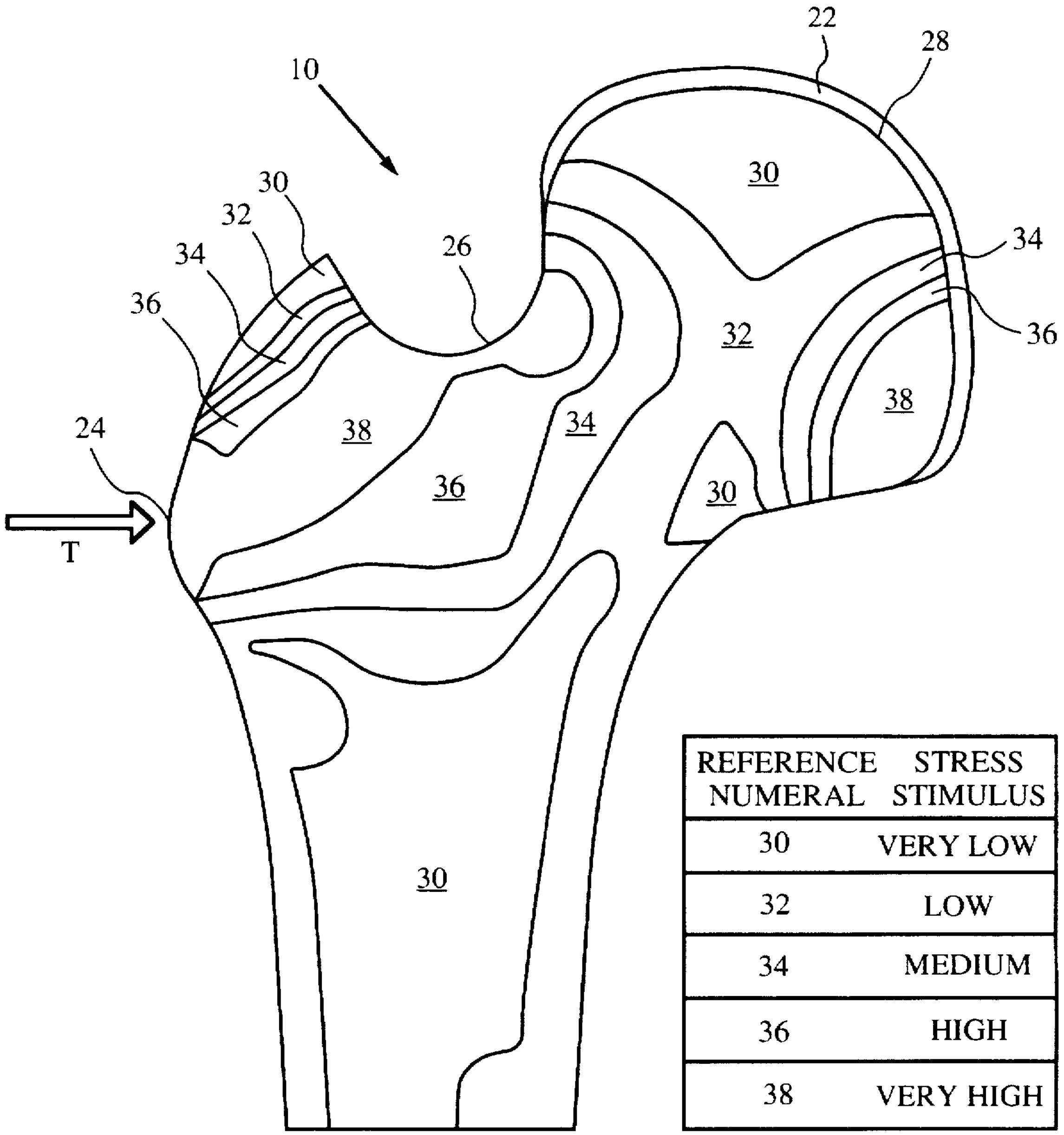
FIG. 3 is a schematic view of the stresses experienced by the femur of FIG. 2 during a traumatic event.
Figure 4:
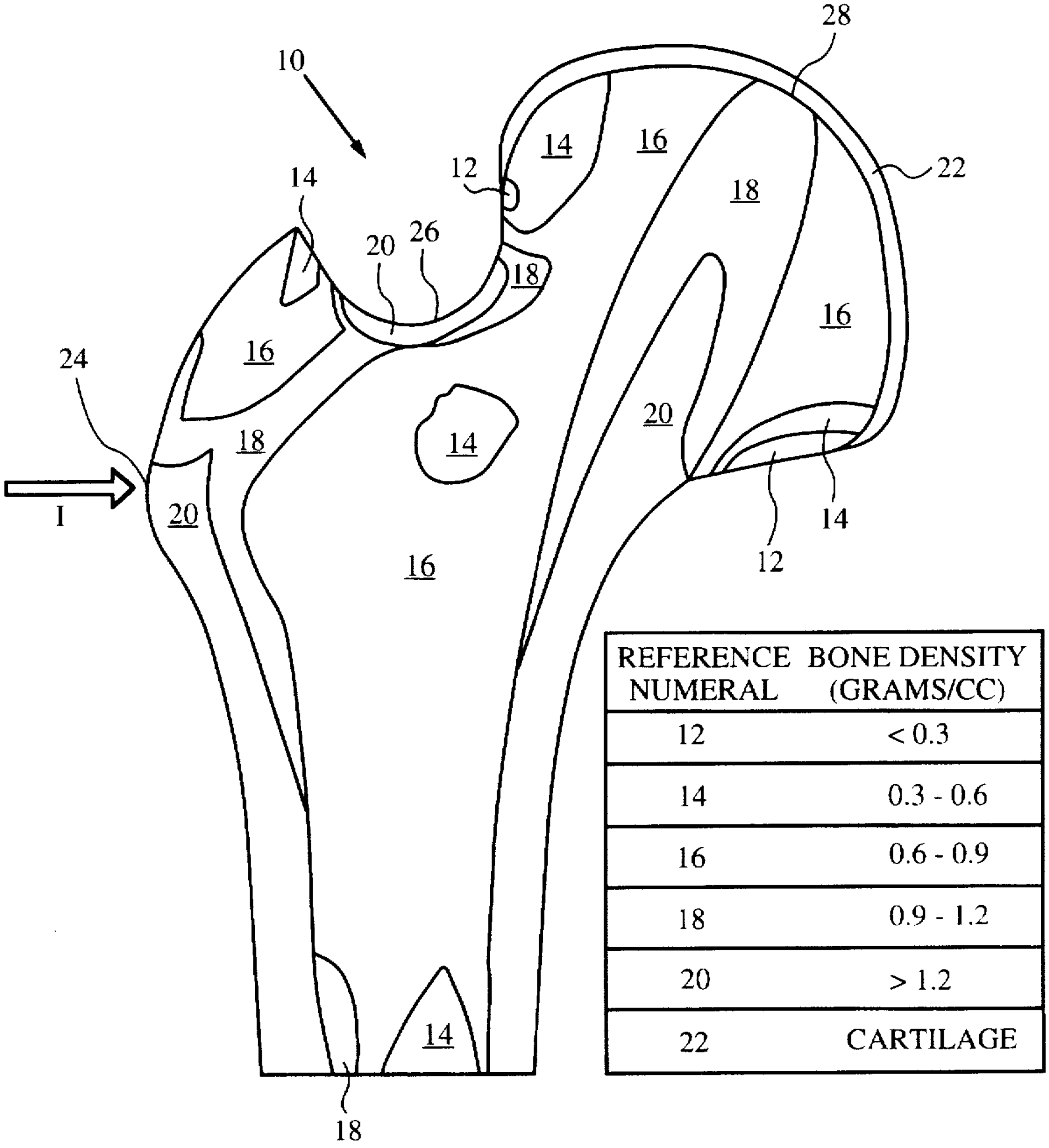
FIG. 4 is a schematic view of the bone density of the femur of FIG. 2 after applying the method and device of the invention.

A preferred method for increasing the fracture resistance of bone tissue to a traumatic force is illustrated in FIGS. 2–4. FIG. 2 is a schematic diagram of the various bone densities found in a bone tissue of a normal adult human before the method of the invention is applied. In this embodiment, the bone tissue is a proximal third of a human femur 10. Femur 10 has particular clinical relevance since a reduction in the number of proximal femur fractures would have substantial benefit to society. It is obvious that the method of the invention could be applied to any bone tissue, but for simplicity, the preferred embodiment focuses on femur 10.

Femur 10 has a greater trochanter 24, a superior femoral neck 26, and a femoral head 28. Femoral head 28 is surrounded by cartilage 22. The distribution of bone densities within femur 10 are indicated by reference numerals 12 through 20 in accordance with the following chart.

| REFERENCE NUMERAL | BONE DENSITY (g/cm$^3$) |
|---|---|
| 12 | <0.3 |
| 14 | 0.3–0.6 |
| 16 | 0.6–0.9 |
| 18 | 0.9–1.2 |
| 20 | >1.2 |

The bone densities of femur 10 between greater trochanter 24 and femoral neck 26 are particularly important since this region of femur 10 experiences the largest stresses during a traumatic event, as will be described in detail below. Between greater trochanter 24 and femoral neck 26, femur 10 has a bone density 14 and a bone density 16 corresponding to densities of 0.3–0.6 grams/cubic cm and 0.6–0.9 grams/cubic cm, respectively.

The bone densities shown in this normal adult femur 10 are insufficient to resist fracture during a traumatic event. FIG. 3 shows the distribution of local stress stimuli experienced by femur 10 during a traumatic event. Because we are focusing on femur 10 in the preferred embodiment, the traumatic event causing the local stress stimuli is a fall to the side. It is obvious that the method of the invention could be applied to increase bone fracture resistance for other types of traumatic events in addition to falls to the side.

During a fall to the side, femur 10 contacts a hard surface, such as a floor (not shown). Contact with the hard surface produces a traumatic force T that is applied to a first location $L_1$. In this example, first location $L_1$ is greater trochanter 24. Traumatic force T has a first direction $D_1$ which is approximately perpendicular to the vertical axis of femur 10. Traumatic force T further has a first magnitude $M_1$. First magnitude $M_1$ is typically 7,000N for a healthy young person of average height and weight. For an older person, first magnitude $M_1$ is typically 3,000N.

The local stress stimuli experienced by femur 10 as a result of traumatic force T are indicated by reference numerals 30 through 38 in accordance with the following chart.

| REFERENCE NUMERAL | STRESS STIMULUS |
|---|---|
| 30 | VERY LOW |
| 32 | LOW |
| 34 | MEDIUM |
| 36 | HIGH |
| 38 | VERY HIGH |

Traumatic force T produces a very high stress stimulus 38 in the region of femur 10 between greater trochanter 24 and femoral neck 26. This is the region where fracture of femur 10 is predicted during a fall. As shown in FIG. 2, femur 10 does not have sufficient bone density in this region to withstand fracture caused by traumatic force T.

By extending the bone remodeling theory presented above, femur 10 can be remodeled to have sufficient bone mass and bone density in the critical areas required to withstand traumatic force T without fracturing. As described in the theory, bone apposition leading to increased bone mass and density occurs when actual daily stress stimulus $\phi_b$ exceeds attractor state stimulus $\phi_{as}$. To increase the fracture resistance of femur 10, actual daily stress stimulus $\phi_b$ must exceed attractor state stimulus $\phi_{as}$ so that bone apposition occurs in the critical areas required to resist fracture from traumatic force T. Actual daily stress stimulus $\phi_b$ exceeds attractor state stimulus $\phi_{as}$ when a non-physiological impulse force I is repeatedly applied to femur 10.

Referring to FIG. 4, non-physiological impulse force I is selected having a second location $L_2$ and a second direction $D_2$ resembling first location $L_1$ and first direction $D_1$, respectively. For the purposes of this discussion, resembling is understood to mean that second location $L_2$ and second direction $D_2$ are sufficiently close to first location $L_1$ and first direction $D_1$, respectively, that the distribution of local stress stimuli experienced by femur 10 as a result of the application of impulse force I is similar to the distribution of local stress stimuli experienced by femur 10 as a result of the application of traumatic force T. The similar distribution of local stress stimuli caused by impulse force I stimulates bone apposition in the critical areas of femur 10 needed to resist fracture due to traumatic force T.

Typically, second location $L_2$ is selected to be within 10 cm of first location $L_1$ and second direction $D_2$ is selected to be within a 20° angle of first direction $D_1$. The preferred location of second location $L_2$ is greater trochanter 24 and the preferred direction of second direction $D_2$ is perpendicular to the vertical axis of femur 10. In addition to second location $L_2$ and second direction $D_2$, impulse force I has a second magnitude $M_2$ significantly smaller than first magnitude $M_1$ of traumatic force T. For the purposes of this discussion, significantly smaller is understood to mean that second magnitude $M_2$ is sufficiently small to ensure that the application of impulse force I to greater trochanter 24 does not cause the fracture of femur 10 we desire to prevent.

In a particularly advantageous embodiment, second location $L_2$, second direction $D_2$, and second magnitude $M_2$ of impulse force I are selected in part by performing a finite element analysis of the bone tissue. The finite element analysis model is described in Beaupré et al. "An Approach for Time Dependent Bone Modeling and Remodeling—Application: A Preliminary Remodeling Simulation", Journal of Orthopedic Research, 8:662–670, 1990, which is incorporated by reference herein. The finite element model (not shown) is a model of femur 10 comprising 1,447 linear quadrilateral and triangular elements and 1,508 nodes.

Using the finite element model, the actual daily stress stimulus $\phi_b$ is calculated for each element of femur 10 in response to applications of various loading conditions on femur 10. The difference between actual daily stress stimulus $\phi_b$ and attractor state stimulus $\phi_{as}$ is then used to calculate the rate of bone apposition and bone resorption for each element in the model. Based on the rates of apposition and resorption for each element in the model, changes in apparent bone density are simulated using a computer, so that the effects of the various loading conditions on the distribution of bone densities in femur 10 may be viewed. By viewing the computer simulation of the various loading effects on bone densities in femur 10, appropriate values of second location $L_2$, second direction $D_2$, and second magnitude $M_2$ are selected.

In addition to the finite element analysis, second location $L_2$, second direction $D_2$, and second magnitude $M_2$ of impulse force I are selected in dependence upon data correlated to the present state of the bone tissue. As described in FIG. 1, part of these data are the three factors that influence a patient's attractor state stimulus $\phi_{as}$: metabolic status 100, genotype 102, and local tissue interaction 104. Information about these factors is gathered in a pretreatment screening of the patient and used to select second location $L_2$, second direction $D_2$, and second magnitude $M_2$ of impulse force I. Additionally, the data correlated to the present state of the bone tissue includes bone geometry and composition 106, as shown in FIG. 1. Bone geometry and composition 106 is determined from a pretreatment radiological measurement of the bone tissue. In an alternative embodiment, bone geometry and composition 106 is determined from a pretreatment ultrasonic measurement of the bone tissue.

Once selected, impulse force I is repeatedly applied to femur 10 at greater trochanter 24 to increase actual daily stress stimulus $\phi_b$. Impulse force I is repeatedly applied during a number of daily treatment sessions so that actual daily stress stimulus $\phi_b$ consistently exceeds attractor state stimulus $\phi_{as}$, as described above, actual daily stress stimulus $\phi_b$ is determined by second magnitude $M_2$ and number of repetitions $n_i$ of impulse force I. Computer simulations performed with a finite element model of a young, healthy person indicate that a second magnitude $M_2$ of 2,000N applied for 1,800 repetitions per day leads to bone deposition in the critical areas of femur 10 that are prone to fracture. By way of reference, 2,000N is approximately the magnitude of loading imposed on femoral head 28 during walking.

The same actual daily stress stimulus $\phi_b$ could be obtained by applying impulse force I with second magnitude $M_2$ of 1,500N for 5,700 repetitions per day. As mentioned above, second magnitude $M_2$ is selected based upon data correlated to the present state of the bone tissue. For safety reasons, patients with lower bone mass undergo treatment with lower applied second magnitude $M_2$ and a reduced number of repetitions $n_i$ per day. In practice, second magnitude $M_2$ generally falls in a range of 100 to 3,000N and number of repetitions $n_i$ generally falls into a range of 1 to 3,600 repetitions.

In applying impulse force I, number of repetitions $n_i$ is important. However the precise frequency of the loading does not play a significant role. For example, 3,000 daily repetitions of impulse force I applied at a frequency of 1 hertz for 3,000 seconds produces the same actual daily stress stimulus $\phi_b$ as 3,000 daily repetitions of impulse force I applied at a frequency of 2 hertz for 1,500 seconds. One advantage of a higher frequency is that less time is required to accumulate the desired number of repetitions $n_i$. For example, in applying 1,800 repetitions of impulse force I, the force could be applied at a frequency of 1 hertz for 30 minutes, 2 hertz for 15 minutes, 3 hertz for 10 minutes, etc.

FIG. 4 shows the bone densities developed in femur 10 as a result of applying impulse force I with second magnitude $M_2$ of 2,000N for 1,800 repetitions per day for 412 days. The results of the repeated application of impulse force I are substantial bone deposition in the region connecting greater trochanter 24 to femoral neck 26. In this region, femur 10 now has bone density 18 and bone density 20, corresponding to a density of 0.9–1.2 grams/cubic cm and a density >1.2 grams/cubic cm, respectively. This is an improvement over the pretreatment bone densities shown in FIG. 2. The region between greater trochanter 24 and femoral neck 26 is the critical area of femur 10 that experiences the highest stresses due to traumatic force T, as shown in FIG. 3. We are able, therefore, to stimulate growth in bone mass and bone density in the critical areas of femur 10 where it is most needed to resist fracture.

Figure 5:
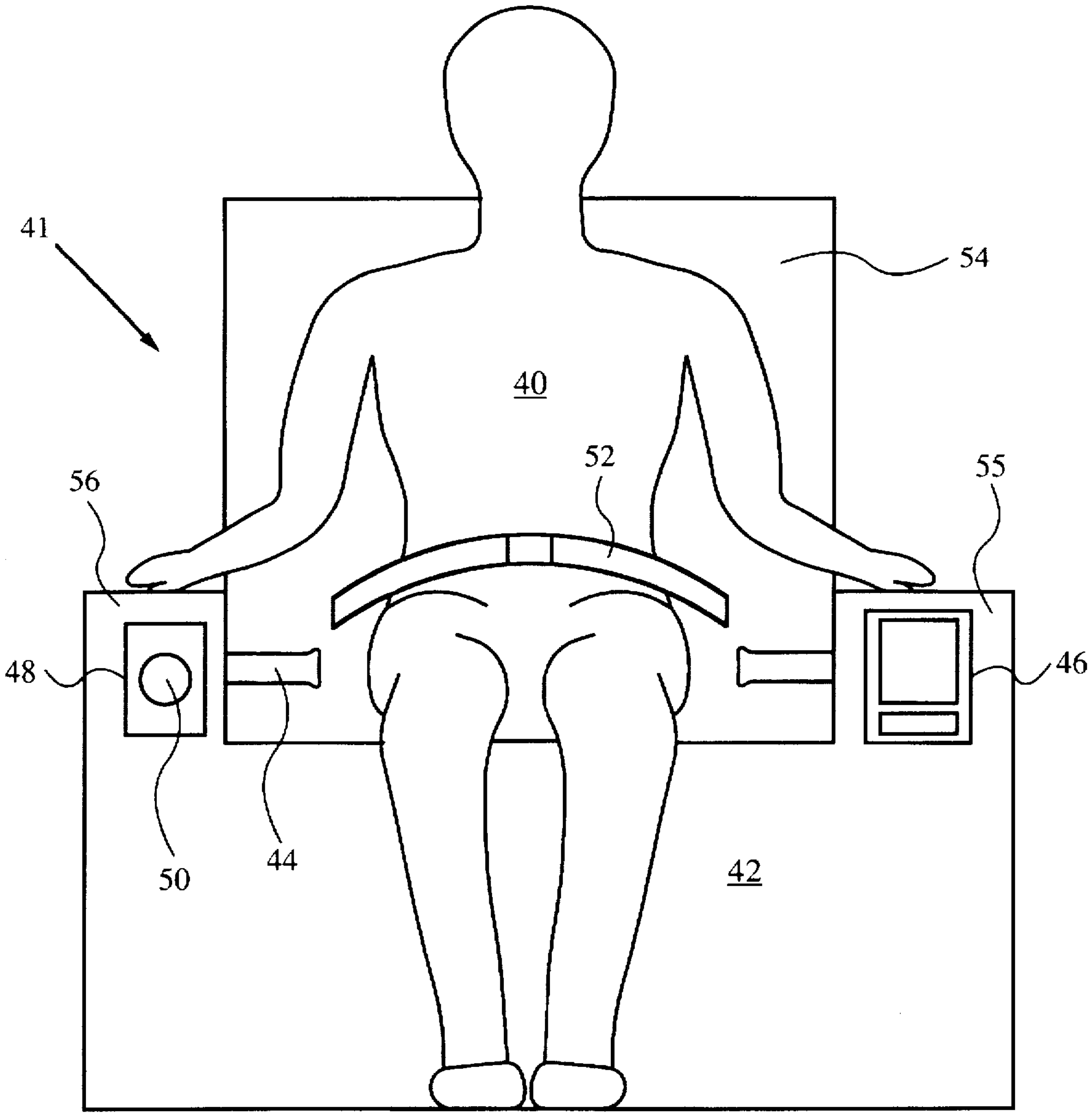
FIG. 5 is a front view of a device for increasing bone fracture resistance according to a preferred embodiment of the invention.

The preferred embodiment of the device used to apply the method of the invention is shown in FIGS. 5–8. Referring to FIG. 5, a device 41 for increasing the fracture resistance of a bone tissue to traumatic force T includes a chair 42 for supporting a seated patient 40. Chair 42 has a back 54 and a restraint 52 for holding patient 40 in a correct position for receiving impulse force I. In the preferred embodiment, restraint 52 is a seat belt fastened around the waist of patient 40. Chair 42 further includes two arms 55 and 56. Each arm 55 and 56 has an impulse force applicator 44.

Figure 6:
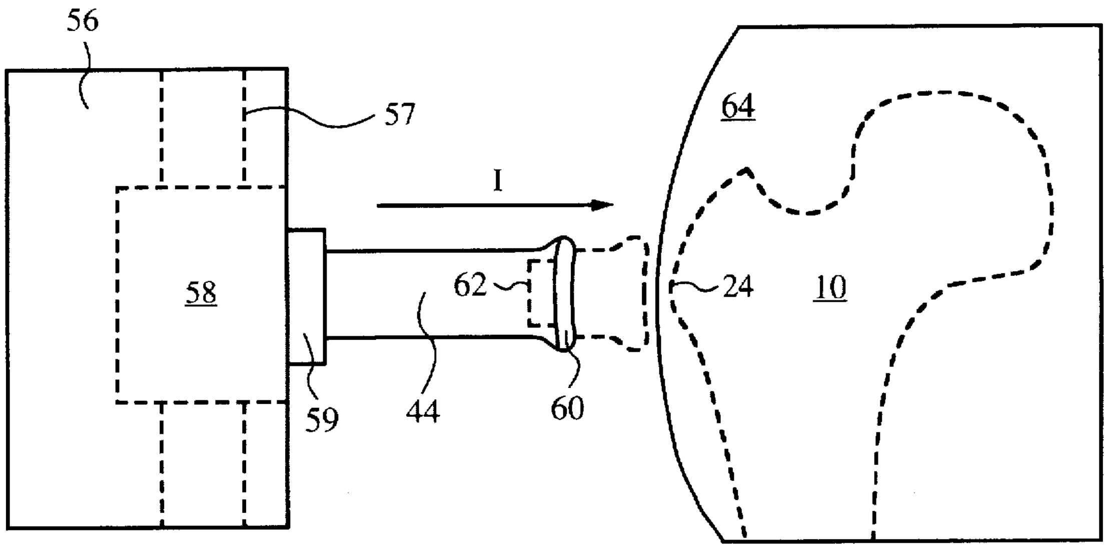
FIG. 6 is a side view of an applicator from FIG. 5 applying an impulse force to a femur.

Applicator 44 and arm 56 are illustrated in greater detail in FIG. 6. Applicator 44 is designed to repeatedly apply impulse force I to femur 10 at second location $L_2$, with second direction $D_2$, and at second magnitude $M_2$. In the preferred embodiment, applicator 44 is a high performance linear actuator commercially available from BE Motion Systems Company, Kimchee Magnetic Division, of San Marcos, Calif. In alternative embodiments, applicator 44 is a pneumatic, hydraulic, or motor driven actuator. Specific techniques of constructing an actuator to deliver a force of consistent location, magnitude, and direction are well known in the art.

Within arm 56, a positioner 58 is mounted on a motorized track 57 such that positioner 58 can slide vertically on track 57. Positioner 58 has a universal joint 59 for holding the base of applicator 44. Positioner 58 is thus designed to adjust the position of applicator 44 relative to femur 10 such that second location $L_2$ and second direction $D_2$ of impulse force I are set by adjusting positioner 58. Applicator 44 further has a padded impact surface 60 for preventing impulse force I from damaging other tissue 64 surrounding femur 10. Below padded impact surface 60 is a feedback sensor 62 connected to the force generator (not shown) of applicator 44. Feedback sensor 62 is for preventing impulse force I from exceeding second magnitude $M_2$. For simplicity, only arm 56 and one applicator 44 are shown in detail in FIG. 6. It is to be understood that arm 55 also has one applicator 44 and one positioner 58 configured in the identical manner, but facing the opposite direction, for applying impulse force I to the other side of patient 40.

Referring again to FIG. 5, a control panel 46 is mounted to an outside surface of arm 55. Control panel 46 is wired to applicator 44 and positioner 58 such that second location $L_2$, second direction $D_2$, and second magnitude $M_2$ are selected through control panel 46. Arm 56 has a safety panel 48 wired to control panel 46. Safety panel 48 includes a button 50 within reach of patient 40. Button 50 is for patient 40 to press to terminate the applications of impulse force I by applicators 44.

Figure 8:
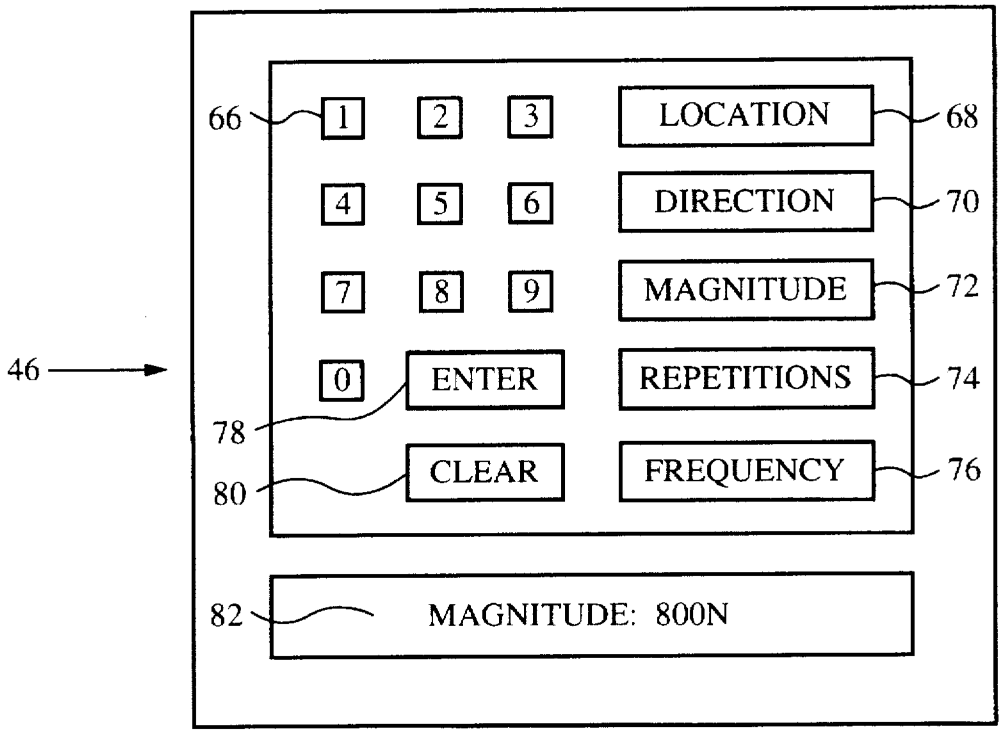
FIG. 8 is a schematic view of the control panel of the device of FIG. 5

Control panel 46 is illustrated in greater detail in FIG. 8. Panel 46 has five function keys for presetting the parameters of the impulse force treatment. The five function keys are a location key 68 for presetting second location $L_2$, a direction key 70 for presetting second direction $D_2$, a magnitude key 72 for presetting second magnitude $M_2$, a repetitions key 74 for presetting number of repetitions $n_i$, and a frequency key 76 for presetting the frequency of the applications. Panel 46 further includes ten digit keys 66 for entering numeric values corresponding to the desired parameters of the impulse force treatment. Below digit keys 66 is an enter key 78 for entering the parameters and a clear key 80 for clearing the parameters entered. Panel 46 also has a display 82 for displaying to the operator the parameters entered.

The operation of the preferred embodiment of device 41 is shown in FIGS. 5–8. Referring to FIG. 5, patient 40 sits in chair 42 and restraint 52 is fastened around the patient's waist. Next, patient 40 or an operator (not shown) enters the desired parameters of the impulse force treatment using control panel 46, as shown in FIG. S. For example, to enter a second magnitude $M_2$ equal to 800N, the operator first presses magnitude key 72, and the word "MAGNITUDE" appears on display 82. Next the operator presses digit keys 66 corresponding to digits 8, 0, and 0 and "800N" appears on display 82. To confirm the entry of second magnitude $M_2$, the operator then presses enter key 78. Each of the remaining four parameters are set in a similar fashion.

Once the five parameters of the impulse force treatment have been entered in control panel 46, positioner 58 positions applicator 44 to apply impulse force I, as shown in FIG. 6. Positioner 58 moves vertically on track 57 and swivels applicator 44 on universal joint 59 so that applicator 44 applies impulse force I at second location $L_2$ in second direction $D_2$ as selected through control panel 46. Next, applicator 44 repeatedly applies impulse force I having second magnitude $M_2$, in this example 800N, to femur 10. During the application of impulse force I, feedback sensor 62 prevents second magnitude $M_2$ from exceeding the preset value of 800N. Applicator 44 continues to apply impulse force I until all of number of repetitions $n_i$ have been delivered. If patient 40 desires to stop the applications of impulse force I at any time during the treatment, he presses button 50.

Figure 7:
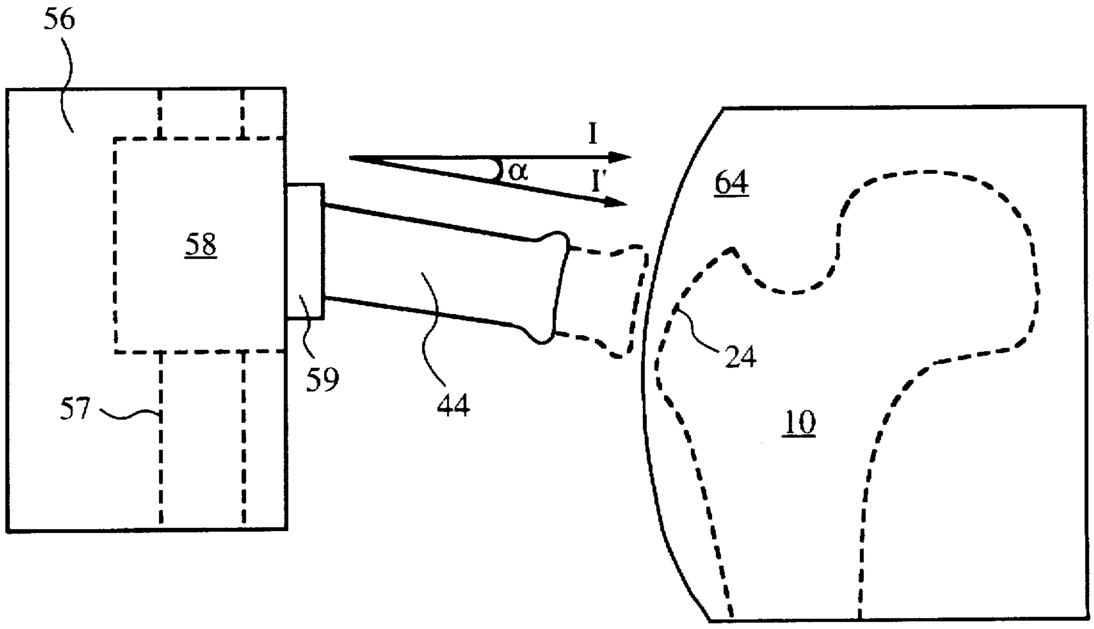
FIG. 7 is a side view of another applicator applying another impulse force to the femur of FIG. 6.

Although padded impact surface 60 lessens any damaging effects the repeated application of impulse force I has on other tissue 64 surrounding femur 10, several other preventative measures are also taken. First, second location $L_2$ and second direction $D_2$ are varied for each treatment session so that padded impact surface 62 impacts a slightly different surface of tissue 64, as shown in FIG. 6 and FIG. 7. Referring to FIG. 6 positioner 58 is positioning applicator 44 to apply impulse force I at a second location $L_2$ which is greater trochanter 24. Further, positioner 58 is positioning applicator 44 to apply impulse force I at a second direction $D_2$ which is perpendicular to the vertical axis of femur 10.

Referring to FIG. 7, positioner 58 has changed the position of applicator 44 so that it is now positioned to apply an impulse force I'. Impulse force I' has a second location $L_2'$ slightly higher on greater trochanter 24 and a second direction $D_2'$ that differs from second direction $D_2$ by angle $\alpha$. In this example, angle $\alpha$ is ten degrees. Varying second location $L_2$ and second direction $D_2$ ensures that patient 40 does not develop skin necrosis or pressure sores as a result of the treatment. Of course, second location $L_2$ and second direction $D_2$ can also be varied during the course of one treatment session in addition to being varied between treatment sessions.

The second method for lessening any damaging effects of impulse force I on tissue 64 is to select a second direction $D_2$ that is approximately perpendicular to the vertical axis of femur 10, as shown in FIG. 6 and described above. Maintaining second direction $D_2$ perpendicular to the vertical axis of femur 10 prevents applicator 44 from applying a shear force and a frictional force to tissue 64.

Figure 9:
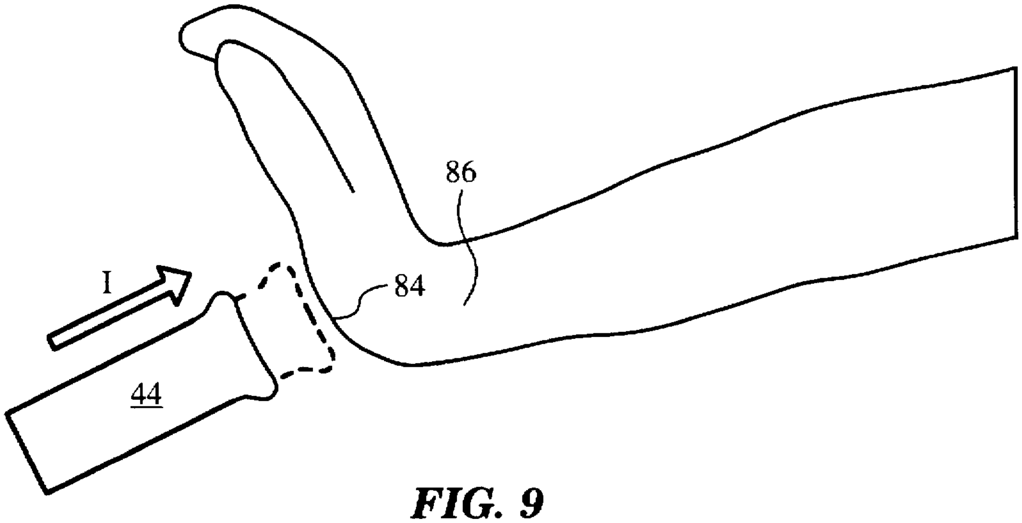
FIG. 9 is a side view of an applicator for increasing the bone fracture resistance of a wrist.

An alternative embodiment of the invention is illustrated in FIG. 9. The primary difference between this embodiment and the preferred embodiment is that this embodiment is designed to increase the fracture resistance of a wrist 86 rather than femur 10. Like femur 10, wrist 86 has particular clinical relevance since a patient often fractures wrist 86 during a traumatic event such as a fall. Applicator 44 is positioned to apply impulse force I at a second location $L_2$ which is a heel 84 of the patient's hand. Second location $L_2$ resembles first location $L_1$ of traumatic force T that is applied to heel 84 when a patient attempts to break his fall and impacts heel 84 on a hard surface, such as a floor (not shown). The repeated application of impulse force I increases the bone density and bone mass in wrist 86, thus making wrist 86 less likely to fracture due to traumatic force T. Other than applying impulse force I to increase the fracture resistance of wrist 86 rather than femur 10, the operation and advantages of this embodiment are identical to the operation and advantages of the preferred embodiment described above.

SUMMARY, RAMIFICATIONS, AND SCOPE

Although the above description contains many specificities, these should not be construed as limiting the scope of the invention but merely as illustrating some of the presently preferred embodiments. Many other embodiments of the invention are possible. For example, the bone tissue to which the impulse force is applied can be tissue from any bone, not just the proximal femur or the wrist. The proximal femur and wrist were illustrated since they are most prone to fracture during a traumatic event. However, the method and device of the invention are just as effective in increasing fracture resistance in other bone tissue. Further, the traumatic force described was for illustrative purposes only. The traumatic force can result from any event, not just a fall to the side. The direction and location of the traumatic force will change based upon the nature of the traumatic event. In these cases, the location and direction of the impulse force selected can easily be changed to increase the fracture resistance of the bone tissue to this different traumatic force.

The device of the invention is shown with a chair for supporting a seated patient. It is obvious that the device could be easily designed to support a patient lying prone, lying supine, lying on their side, etc. Additionally, the impulse force applicators can have different shapes and sizes than those illustrated to apply impulse forces to different areas of the patient's body. Further, the applicators can be powered by a pneumatic, hydraulic, or other type of engine.

Also, the device can have more than one applicator on each side for applying forces to the patient's bone tissue.

In another embodiment of the invention, the restraint for holding the patient in a correct position for receiving an impulse force is eliminated. Instead, the second direction of the impulse force is adjusted so that the patient is pressed slightly into the seat as the forces are applied, eliminating the need for the restraint.

Therefore, the scope of the invention should be determined, not by examples given, but by the appended claims and their legal equivalents.

We claim:

1. A device for increasing the fracture resistance of a bone tissue to a traumatic force, the traumatic force having a first location, a first direction, and a first magnitude, the device comprising:

a) application means for repeatedly applying to the bone tissue a nonphysiological impulse force having a second location and a second direction resembling the first location and the first direction, respectively, but having a second magnitude significantly smaller than the first magnitude; and b) positioning means for positioning the application means relative to the bone tissue while the nonphysiological impulse force is repeatedly applied such that the bone tissue experiences the nonphysiological impulse force;

wherein the application means includes feedback means for preventing the nonphysiological impulse force from exceeding the second magnitude.

2. The device of claim 1, further comprising selective control means for controlling the application means and the positioning means such that the second location, the second direction, and the second magnitude are selected through the selective control means.

3. The device of claim 2, wherein the selective control means further comprises means for controlling a number of repetitions of the nonphysiological impulse force and a frequency of the repetitions.

4. The device of claim 2, further comprising a safety system connected to the selective control means, wherein the safety system includes means for terminating the application of the nonphysiological impulse force.

5. The device of claim 1, wherein the application means has a padded impact surface for preventing the nonphysiological impulse force from damaging other tissue surrounding the bone tissue.

6. A device for increasing the fracture resistance of a bone tissue to a traumatic force, the traumatic force having a first location, a first direction, and a first magnitude, the device comprising:

a) application means for repeatedly applying to the bone tissue a nonphysiological impulse force having a second location and a second direction resembling the first location and the first direction, respectively, but having a second magnitude significantly smaller than the first magnitude;

b) positioning means for positioning the application means relative to the bone tissue while the nonphysiological impulse force is repeatedly applied such that the bone tissue experiences the nonphysiological impulse force;

c) selective control means for controlling the application means and the positioning means such that the second location, the second direction, and the second magnitude are selected through the selective control means; and d) a safety system connected to the selective control means, the safety system including means for terminating the application of the nonphysiological impulse force.

7. The device of claim 6, wherein the selective control means further comprises means for controlling a number of repetitions of the nonphysiological impulse force and a frequency of the repetitions.

8. The device of claim 6, wherein the application means includes feedback means for preventing the nonphysiological impulse force from exceeding the second magnitude.

9. The device of claim 6, wherein the application means has a padded impact surface for preventing the nonphysiological impulse force from damaging other tissue surrounding the bone tissue.

10. A method of increasing the fracture resistance of a bone tissue to a traumatic force having a first location, a first direction, and a first magnitude, said method comprising the following steps:

a) selecting a nonphysiological impulse force having a second location and a second direction resembling said first location and said first direction, respectively, but having a second magnitude that is significantly smaller than said first magnitude; and b) repeatedly applying said nonphysiological impulse force to said bone tissue; whereby said bone tissue is stimulated to grow bone mass in critical areas of said bone tissue where stresses from said traumatic force are largest.

11. The method of claim 1, wherein said second location, said second direction, and said second magnitude are selected in part by performing a finite element analysis of said bone tissue.

12. The method of claim 1, wherein said second location, said second direction, and said second magnitude are selected in dependence upon data correlated to the present state of said bone tissue.

13. The method of claim 12 wherein said data comprises information about the genotype and metabolic status of a patient to whom said bone tissue belongs.

14. The method of claim 12 wherein said data comprises a radiological measurement of said bone tissue.

15. The method of claim 12 wherein said data comprises an ultrasonic measurement of said bone tissue.

16. The method of claim 1, wherein said nonphysiological impulse force is repeatedly applied during a plurality of treatment sessions.

17. The method of claim 1, wherein said nonphysiological impulse force is repeatedly applied for a number of repetitions in a range of 1 to 3600 repetitions.

18. The method of claim 1, wherein said second magnitude is in a range of 100 to 3000N.

19. The method of claim 1, wherein the repeated application of said nonphysiological impulse force further comprises varying said second location to avoid damaging other tissue surrounding said bone tissue.

20. The method of claim 1, wherein said second direction is approximately perpendicular to a surface of said bone tissue to prevent a shear force and a frictional force from damaging other tissue surrounding said bone tissue.

21. The method of claim 1, wherein said bone tissue comprises a portion of a femur.

22. The method of claim 1, wherein said bone tissue comprises a portion of a wrist.

* * * * *